United States Patent [19]
Raulerson

[11] Patent Number: 4,666,438
[45] Date of Patent: May 19, 1987

[54] NEEDLE FOR MEMBRANE PENETRATION

[76] Inventor: J. Daniel Raulerson, 1203 Belleville Ave., Brewton, Ala. 36426

[21] Appl. No.: 751,015

[22] Filed: Jul. 2, 1985

[51] Int. Cl.$^4$ .............................................. A61M 27/00
[52] U.S. Cl. ..................................... 604/272; 604/164
[58] Field of Search .............................. 604/272–274, 604/160, 164, 166, 168

[56] References Cited

U.S. PATENT DOCUMENTS

| | | | |
|---|---|---|---|
| 2,711,733 | 6/1955 | Jacoby, Jr. | 604/274 |
| 3,030,953 | 4/1962 | Koehn | 604/168 |
| 3,308,822 | 3/1967 | De Luca | 604/274 |
| 3,352,306 | 11/1967 | Hirsch | 604/168 |
| 3,459,189 | 8/1969 | Alley et al. | 604/168 |
| 3,788,320 | 1/1974 | Dye | 604/272 |
| 3,960,153 | 6/1976 | Carey et al. | 604/164 |
| 4,037,600 | 7/1977 | Poncy et al. | 604/160 |

Primary Examiner—Stephen C. Pellegrino
Attorney, Agent, or Firm—A. W. Fisher, III

[57] ABSTRACT

A needle specifically configured to enhance membrane penetration comprising an inner solid substantially cylindrical body including a longitudinally disposed fluid aspiration channel formed in the upper surface thereof and an outer penetration tip formed on the outer portion of the inner solid substantially cylindricla body, the penetration tip including a longitudinally disposed concave fluid recess extending between a penetration point formed on outer end thereof and the upper surface of the inner solid substantially cylindrical body rearward of the outermost end of the longitudinally disposed fluid aspiration channel and a pair of planar surfaces formed on opposite sides of the penetration tip and the solid substantially cylindrical body, the pair of planar surfaces converging forwardly to the penetration point and diverging upwardly to the outer portion of the longitudinally disposed concave fluid recess to intersect a pair of arcuate cutting edges diverging upwardly and rearwardly from the penetration point.

16 Claims, 9 Drawing Figures

NEEDLE FOR MEMBRANE PENETRATION

BACKGROUND OF THE INVENTION

1. Field of the Invention

A needle specifically configured to enhance membrane penetration comprising a solid substantially cylindrical body having a penetration tip formed on the outer portion thereof.

2. Description of the Invention

It is usual practice in blood transfusions, intraveneous feeding or when fluids are to be withdrawn from the body to attach a tube to a hollow needle and insert the needle into a vein or other body cavity. The fluid then flows through the tube and hollow needle into or from the body.

Repeated punctures of veins with metal needles for withdrawing successive blood samples, delivering successive transfusions or intravenous feeding tend to cause venous thromboses and subcutaneous hematomas. To reduce such tramma, a common practice is to leave the needle in the body. Unfortunately, relative movement between the body and needle creates a continuing problem.

Thus, insertion of the soft flexible catheter into the body cavity or vein is desirable. This may be accomplished by inserting the end of the soft flexible catheter into the vein or body cavity by means of a needle and then withdrawing the needle. This is generally accomplished by using a relatively large hollow needle to form an incision, telescoping the soft flexible catheter through the hollow needle and then withdrawing the needle over the soft flexible catheter. Such a method of inserting a catheter tube produces a large incision and excessive cutting of the tissue. This is particularly undesirable when the incision is made in a vein. Such procedures are often painful and produce a coring effect.

Another such procedure may comprise the insertion of the catheter into the body cavity or vein by placing the catheter over a needle inserted into the body cavity or vein and then withdrawing the needle. This procedure or technique exhibits the same limitations and drawbacks as the technique previously described.

Thus, there is a need for an improved tissue piercing point, to reduce the penetration force required thereby minimizing the pain incident to the incision and substantially eliminating coring.

The following are examples of the prior art: U.S. Pat. No. 2,560,162; U.S. Pat. No. 2,716,983; U.S. Pat. No. 2,770,236; U.S. Pat. No. 2,282,744; U.S. Pat. No. 3,030,953; U.S. Pat. No. 3,067,742; U.S. Pat. No. 3,308,822; U.S. Pat. No. 3,477,423; U.S. Pat. No. 3,788,320; U.S. Pat. No. 3,893,445; U.S. Pat. No. 4,020,837 and French No. 1,225,009.

SUMMARY OF THE INVENTION

The present invention relates to a needle for use in placing an intravenous catheter configured to enchance tissue penetration. More specifically, the needle comprises an inner solid substantially cylindrical body having an outer penetration tip formed on the outer portion thereof.

The inner solid substantially cylindrical body includes a longitudinally disposed fluid aspiration channel formed on the surface thereof.

The penetration tip includes a longitudinally disposed concave recess that extends outwardly from the outer portion of the longitudinally disposed fluid aspiration channel to a penetration point formed on the outermost portion thereof formed by a pair of planar surfaces formed on opposite sides of the inner solid substantially cylindrical body and the penetration tip.

In use, the needle is placed into the outer end of a catheter. Once so positioned, the needle is addressed with the vein or body cavity. The penetration point is then inserted into the vein or body cavity to penetrate the skin. Application of continued pressure causes the pair of forwardly converging cutting edges to cut the skin and body tissue in a substantially V-shaped cross-section as the needle enters the patient's body. A smooth transition region minimizes additional trauma as the inner solid substantially cylindrical body enters the patient's body. The blood or fluid is aspirated between the needle and the outer end of the catheter through the longitudially disposed concave recess and the longitudially disposed fluid aspiration channel.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

As shown in FIGS. 1 through 4, the present invention relates to a needle indicated as 10 for use in placing on intravenous catheter comprising an inner solid substantially cylindrical body generally indicated as 12 having an outer penetration tip generally indicated as 14 formed on the outer portion thereof.

Figure 5:
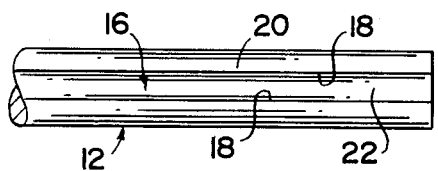
FIG. 5 is a top view of the needle after the first grind.
Figure 6:
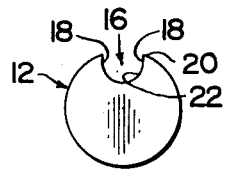
FIG. 6 is an end view of the needle after the first grind.

As best shown in FIGS. 1 and 4 through 9, the inner solid substantially cylindrical body 12 includes on longitudinally disposed fluid aspiration channel generally indicated as 16 formed therein. The longitudinally disposed fluid aspiration channel 16 formed by the first grind as shown in FIGS. 5 and 6 comprises a pair of substantially parallel side walls each indicated as 18 extending inwardly from the periphery or upper surface of 20 of the inner solid substantially cylindrical body 12 terminating in a substantially arcuate or U-shaped surface 22. Of course, the longitudinally disposed fluid aspiration channel 16 may comprise a V-shaped or other cross-section configuration.

Figure 7:
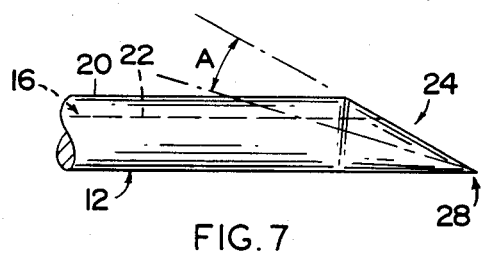
FIG. 7 is a side view of the needle after the second grind.
Figure 4:
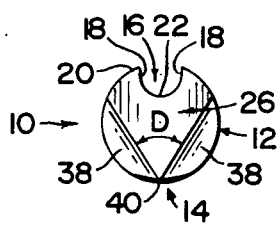
FIG. 4 is a diagrammatic end view of the needle.

As shown in FIG. 7, the second grind forms a conical shape generally indicated as 24 having the major axis inclined at fifteen degrees relative to the conical surface thereof shown as the included angle A of fifteen degrees.

Figure 1:
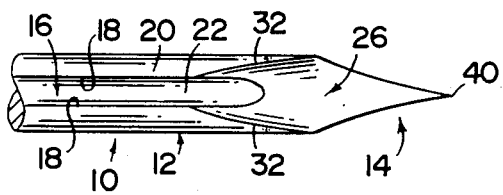
FIG. 1 is a top view of the needle.
Figure 8:
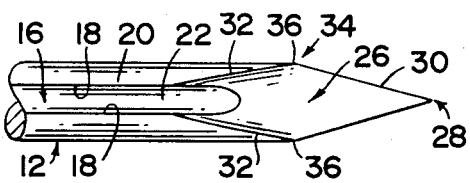
FIG. 8 is a top view of the needle after the third grind.
Figure 9:
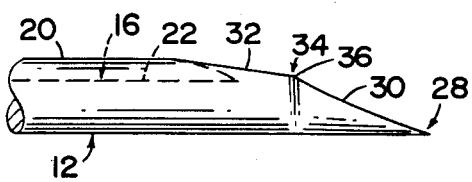
FIG. 9 is a side view of the needle after the third grind.

As shown in FIGS. 8 and 9, the third grind forms a longitudinally disposed concave recess 26 extending outwardly from the outer portion of the longitudinally disposed aspiration channel 16 to the outer end 28 of the conically shape 24 cooperatively forming a pair of forwardly converging cutting edges each indicated as 30. The major axis of the longitudinally disposed concave recess 26 is inclined at fifteen degrees relative to the longitudinal axis of the inner solid substantially cylindrical body 12 shown as the included angle B of fifteen degrees. A pair of forwardly diverging edges 32 extend from the outer portion of the longitudinally disposed fluid aspiration channel 16 to intersect the corresponding forwardly converging cutting edges 30 to cooperatively form a transition region 34 having a pair of smooth transition points each indicated as 36. As best shown in FIGS. 1 and 8, the outer end 28 of the longitudinally disposed fluid aspiration channel 16 extends into the longitudinally disposed concave recess 26. The ratio of the diameter of the longitudinally disposed concave recess 26 to the diameter of the inner solid substantially cylindrical body 12 is 1.3 to 1.0.

Figure 2:
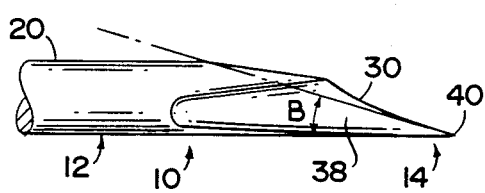
FIG. 2 is a side view of the needle.
Figure 3:
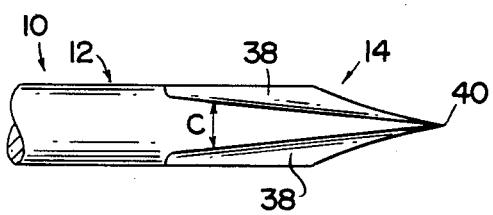
FIG. 3 is a bottom view of the needle.

As best shown in FIGS. 2 and 3, the fourth grind forms a pair of planar surfaces each indicated as 38 formed on opposite sides of the inner solid substantially cylindrical body 12 and the conically shape 24. The planar surfaces 38 are inclined relative to each other such that the planar surfaces 38 converge in the horizontal plane to intersect each other with an included angle of sixteen degrees indicated as C and the outer end of the longitudinally disposed concave recess 26 to cooperatively form a penetration point 40 and diverge in the vertical plane to forming an included angle of fifty degrees indicated as D to intersect opposite sides of the longitudinally disposed concave recess 26 at the pair of forwardly converging cutting edges 30. As best shown in FIGS. 1 and 2, the cutting edges 30 are arcuate or concave in configuration. Although the needle 10 has been described in part with reference to multiple grinds, other means of production may be employed.

In use, the needle 10 is placed into the outer end of a catheter (not shown). Once so positioned, the needle 10 is addressed wih the vessel or body cavity. The penetration point 40 is then inserted into the vessel or body cavity to penetrate the skin. The application of continued pressure causes the pair of forwardly converging cutting edges 30 to cut into skin and body tissue in a substantially V-shaped cross-section. As the needle 10 enters the patient's body the smooth transition region 34 minimizes additional trauma as the inner solid substantially cylindrical body 12 enters the patient's body. The blood or fluid is aspirated between the needle 10 and the outer end of the catheter (not shown) through the longitudinally disposed concave recess 26 and the longitudinally disposed fluid aspiration channel 16.

Comparative testing of the instant needle 10 and a standard ANGIOCATH 18 gauge catheter and needle combination using a 6 millimeter polyethelene membrane material revealed needle 10 penetration force is 16% better than the ANGIOCATH at 90 degrees and 40% better at 30 degrees while the catheter tip penetration of the needle 10 is 15% better than the ANGIOCATH at 90 degrees and 26% better at 30 degrees.

The present invention has been described for use in placing a catheter (not shown). It is envisioned that the structure has similar application and use with biopsy procedures and certain industrial testing techniques.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, what is claimed is:

1. A needle specifically configured to enhance membrane penetration comprising an inner solid body including a fluid channel formed in the surface thereof and an outer penetration tip formed on the outer portion of said inner solid body, said penetration tip including a longitudinally disposed concave recess extending between a penetration point formed on an outer end thereof and the upper surface of said inner solid body, said penetration tip cooperatively formed by a pair of planar converging surfaces formed on opposite sides of said inner solid body, said pair of planar surfaces converge forward to said penetration point and diverge upwardly to intersect opposite sides of said longitudinally disposed concave recess to form a pair of cutting edges, each of said pair of cutting edges concave in both the horizontal and vertical planes relative to the longitudinal axis of said inner solid body.

2. The needle of claim 1 wherein said inner solid body is substantially cylindrical in configuration.

3. The needle of claim 2 wherein the ratio of the diameter of the longitudinally disposed concave recess to the diameter of the inner solid substantially cylindrical body is substantially 1.3 to 1.

4. The needle of claim 1 wherein the horizontal included angle formed between said pair of planar surfaces is substantially sixteen degrees.

5. The needle of claim 4 wherein the vertical included angle formed between said pair of planar surface is substantially fifty degrees.

6. The needle of claim 1 further including the transition region comprising a pair of forwardly diverging edges extending from opposite sides of said longitudinally disposed fluid aspiration channel to intersect said forwardly converging cutting edges.

7. The needle of claim 6 wherein said pair of forwardly diverging edges extend downwardly from opposite sides of said longitudinally disposed fluid aspiration channel to intersect said forwardly converging cutting edges.

8. The needle of claim 1 wherein said outer penetration tip has a major axis inclined relative to the longitudinal axis of said inner solid body.

9. The needle of claim 1 wherein the included angle between said major axis and said longitudinal axis is substantially fifteen degrees.

10. The needle of claim 9 wherein said longitudinally disposed concave recess has a major axis included relative to the longitudinal axis of said inner solid body.

11. The needle of claim 10 wherein the inclined angle between said major axis and said longitudinal axis is substantially fifteen degrees.

12. The needle of claim 1 wherein said inner solid body further includes a longitudinally disposed fluid aspiration channel formed in the upper surface thereof.

13. The needle of claim 12 wherein said longitudinally disposed fluid aspiration channel is substantially U-shaped in configuration.

14. The needle of claim 12 wherein said longitudinally disposed concave recess extends between said penetration point and the upper surface of said inner solid body rearward of the outer portion of said longitudinally disposed fluid aspiration channel.

15. A needle specifically configured to enhance membrane penetration comprising an inner solid body including a fluid aspiration channel formed on the upper surface of said body and an outer penetration tip formed on the outer portion of said inner solid body, said penetration tip including a longitudinally disposed concave recess extending between a penetration point formed on outer end thereof and the upper surface of said inner solid body, said penetration point cooperatively formed by a pair of planar converging surfaces formed on opposite sides of said inner solid body, said pair of planar surfaces converge forward to said penetration point and diverge upwardly to intersect the outer portion of said longitudinally disposed concave recess to form a pair of cutting edges and a transition region comprising a pair of forwardly diverging edges extending downwardly from opposite sides of said fluid aspiration channel to intersect the origin of said forwardly converging cutting edges opposite said penetration tip.

16. The needle of claim 15 wherein each of said pair of cutting edges are concave in both the horizontal and vertical planes relative to the longitudinal axis of said inner solid body.

* * * * *